(12) United States Patent
Stormo (10) Patent No.: US 6,346,412 B1
(45) Date of Patent: Feb. 12, 2002

(54) MICROBIAL REMEDIATION REACTOR AND PROCESS

(75) Inventor: Keith E. Stormo, Moscow, ID (US)

(73) Assignee: Newbio, Inc., Wayzata, MN (US)

( * ) Notice: Subject to any disclaimer, the term of this patent is extended or adjusted under 35 U.S.C. 154(b) by 0 days.

(21) Appl. No.: 09/254,309

(22) PCT Filed: Sep. 3, 1997

(86) PCT No.: PCT/US97/15558

§ 371 Date: Mar. 3, 1999

§ 102(e) Date: Mar. 3, 1999

(87) PCT Pub. No.: WO98/09919

PCT Pub. Date: Mar. 12, 1998

(51) Int. Cl.$^7$ ................................................ C12S 13/00
(52) U.S. Cl. .................... 435/262; 435/262.5; 210/616; 422/227; 588/207
(58) Field of Search .............................. 435/262, 262.5, 435/299.1, 297.2, 289.1; 210/615, 616, 621, 622, 791–796, 767, 293, 263, 500.1; 588/202, 206, 207; 266/44, 235, 233; 422/227, 231

(56) References Cited

U.S. PATENT DOCUMENTS

| | | | |
|---|---|---|---|
| 1,478,222 A | 12/1923 | Hansen .................... 366/170.3 |
| 1,527,404 A | 2/1925 | Haller et al. .............. 366/170.3 |
| 3,152,982 A | 10/1964 | Pagnotti ........................ 210/7 |
| 4,728,082 A | 3/1988 | Emmett, Jr. et al. ......... 266/168 |
| 4,732,608 A | 3/1988 | Emmett, Jr. et al. ...... 75/101 R |
| 4,974,816 A | 12/1990 | Emmett, Jr. et al. ........ 266/168 |
| 5,007,620 A | 4/1991 | Emmett, Jr. et al. ........ 266/168 |
| 5,034,131 A | 7/1991 | Stenroos et al. ............ 210/612 |
| 5,055,204 A | 10/1991 | Bogart ........................ 210/758 |
| 5,057,284 A | 10/1991 | Emmett, Jr. et al. ........ 422/225 |
| 5,061,080 A | 10/1991 | MacKay et al. .......... 366/168.2 |
| 5,102,803 A | 4/1992 | Weaver ........................ 422/184 |
| 5,227,136 A | 7/1993 | Hanify et al. ................ 422/277 |
| 5,342,429 A | 8/1994 | Yu et al. ....................... 266/235 |
| 5,616,304 A | 4/1997 | Stormo .......................... 422/227 |
| 5,744,105 A | 4/1998 | Stormo .......................... 422/227 |
| 5,779,996 A | 7/1998 | Stormo .......................... 422/227 |

OTHER PUBLICATIONS

"Anaerobic Remediation of Dinoseb from Contaminated Soil", Roberts, Kaake, Funk, Crawford, and Crawford, *Applied Biochemistry and Biotechnology*, vol. 39/40, 1993;.

"Effect of the Addition of Microbial Surfactants on Hydrocarbon Degradation in a Soil Population in a Stirred Reactor", Oberbremer, Muller–Hurtig, & Wagner, *Appl Microbiol Biotechnol* (1990) 32:485–489;.

(List continued on next page.)

*Primary Examiner*—William H. Beisner
(74) *Attorney, Agent, or Firm*—Pedersen & Company, PLLC; Ken J. Pedersen; Barbara S. Pedersen (57) ABSTRACT

Embodiments of a remediation reactor and mixer/contactor blade for the reactor are shown and described, the reactor (11) being for containing a liquid slurry, suspension or settled bed of solid particles containing microorganisms. Inside the vessel is a supply conduit and at least one generally horizontal stirrer blade (27) in fluid connection with the supply conduit. The stirrer blade is a mixer/contactor which has a leading side having openings through which fluid may pass. The stirrer blade rotates in the vessel, and this rotation is made easier by the hydraulic forces of fluid flowing out from the stirrer blade. The flowing fluid creates a fluidization zone in the slurry, suspension or settled bed at or near the leading edge of the stirrer blade. The fluidization zone is less dense than the rest of the sediment bed, and the stirrer blade tends to rotate into the fluidization zone. This way, controlled rotation of the stirrer blade may be created near the bottom of the vessel, enhancing mixing of the microorganisms with the slurry, suspension or settled bed in the vessel, without unnecessarily damaging the microorganisms, especially when the flowing fluid contains contaminants which are nutrients for the microorganisms.

20 Claims, 9 Drawing Sheets

OTHER PUBLICATIONS

"Bioremediation of Hazardous Wastes in a Slurry Reactor, The EIMCO Biolift® Reactor", Brox & Hanify, Presented at the ASME Winter Annual Meeting, 5$^{th}$ Annual Bioprocess Engineering Program Symposuim, in Atlanta, GA, Dec. 2–4, 1991;.

"MGP Soil Remediation in a Slurry–Phase System: A Pilot–Scale Test", Liu, Srivastava, Paterek, & Pradhan, Pope, Hayes & Linz, Jerger, prior to Sep. 1994;.

"Removal of Creosote from Soil by Bioslurry Reactors", Lauch & Hermann, Mahaffey & Jones, Dosani & Hessling, *Environmental Progress* (vol. 11, No. 4), Nov., 1992;.

"SITE Demonstration of Slurry–Phase Biodegradation of PAH Contaminated Soil", Lewis, *Air & Waste*, vol. 43, Apr. 1993;.

"Demonstration of the J.R. Simplot Ex Situ Bioremediation Technology for Treatment of Nitroaromatic Contaminants at the Bowers Field Site in Ellensburg, Washington", *EPA Fact Sheet*, Aug. 1993;.

"EIMCO Reactors—Load 'em Up, Move it Out", *The Bioremediation Report*, Sep. 1992;.

"Dynamic Response of Naphthalene Biodegradation in a Continuous Flow Soil Slurry Reactor", DeGrazia, King, Blackburn, Applegate, Bienkowski, Hilton & Sayler, *Biodegradation* 2, 81–91, 1991;.

"Three Phase Slurry Reactors", Chaudhari & Ramachandran, *AIChE Journal* (vol. 26, No. 2), Mar. 1980;.

"Application of IGT's MGP–REM Process in Landfarming Mode", Kelley, Srivastava, Conrad Paterek & Liu, Nelson, Hayes & Linz, Prior to Sep. 1994;.

"Feasibility of Biodegrading TNT—Contaminated Soils in a Slurry Reactor", Montmagno & Irvine, Jun. 1990.

Stormo, K.E. and Deobald, L.A., "Novel Slurry Bioreactor with Efficient Operation and Intermittent Mixing Capabilities", *Biological Unit Processes for Hazardous Waste Treatment*, edited by Hinchee, Oct., 1995, pp. 129–135.

Copy of Poster Board Presentation at the Third International In–Situ and On–Site Bioremediation Symposium, San Diego, California, Apr. 25–26, 1995.

MICROBIAL REMEDIATION REACTOR AND PROCESS

BACKGROUND OF THE INVENTION

1. Field of the Invention

This invention relates to microbial reactors and to microbial reactor systems in general, and more specifically, to a mixer/contactor for a slurry, suspension or settled bed reactor system. The mixer/contactor is advantageous for processes wherein contact time may be relatively long, and/or wherein minimum energy input for suspending and mixing solid particles in the slurry, suspension or settled bed is desired, for example, in the biological remediation of liquid waste streams or contaminated sludges or soils.

2. Related Art—Soil Remediation

Slurry or suspension or settled bed reactors are commonly used for processing ores, soils, and wood chips. Also, they are commonly used to effect the biological, enzymatic or chemical conversion of soluble and insoluble reactants. A slurry or suspension is a mixture of a liquid and solid particles, wherein at least a portion of the solid particles are suspended in the liquid. In a slurry or suspension reactor, a portion of the solid particles may be settled in the bottom of the reactor to form a bed.

There is a large need for conversion of contaminants, especially chemical contaminants, found in liquid waste streams, sludges and soils. These chemicals may be organic or inorganic, and hazardous or toxic. Many millions of cubic feet of soils contaminated with these chemicals exist throughout the world and are in need of remediation.

Biodegradation of many of these contaminating chemicals has been conducted. "Biodegradation" means breaking down these chemicals to less hazardous or less toxic reaction products via biological pathways using microorganisms. The microorganisms, or "microbes", may operate aerobically, microaerophylically or anaerobically, or in any combination thereof. Also, the microorganisms may operate via oxidative pathways or reductive pathways. Microorganisms include bacteria, protozoa, fungi and algae. Biodegradation of soils contaminated with chemicals is one way to remediate the soil.

Often, the remediating microorganisms operate on the soil contaminating chemicals in a slurry environment in a reactor vessel, wherein the soil is mixed with water to at least partially suspend the soil particles for intimate contact with the microorganisms. To further increase suspension, mixing and contacting, a gas, such as air in aerobic applications, for example, may be added to the reactor vessel. When the reactor vessel contains microorganisms and a slurry, it is referred to as a bioslurry reactor.

Presently, at least four bioslurry reactor systems are being commercialized for soil remediation. The first system, developed by MOTEC, Inc. of Mt. Juliet, Tenn., involves technology adapted for treatment of pesticides, PCB's, dioxin and halogenated and nonhalogenated organic compounds. While demonstrated to be effective for treating sludge, liquids and soils having high organic concentrations, the MOTEC process has been reported to be less suitable for use with inorganic-laden wastes.

The MOTEC technology, which is a sequential process, is also referred to as liquid solid contact digestion (LSCD). The system involves two to three tank digestor which are aerated using air spargers and are agitated using turbine mixers. Alternatively, this technology may be adapted, by use of high shear propeller mixers, to enhance aerobic biological degradation in lagoons.

The second technology, developed by Detox Industries, Inc. of Sugarland, Tex., is intended for use in treating chlordane, myrex, oil, phenolics, polycyclic aromatic hydrocarbons, creosote, pentachlorophenol (PCP) and polychlorinated biphenyls (PCB's). The Detox system includes an open-topped reaction tank or on-site created lagoon that utilizes a synthetic liner. The tank is adapted to retain a slurry and is fitted with air distributors.

Another bioslurry reactor, consisting of several agitated and aerated vessels, has been used in a pesticide spill application by ECOVA of Redmund, Wash.

The MOTEC, Detox, and ECOVA systems described above are operated in batch mode. After the placement of contaminated soil and water into the reactor vessel, the vessel is aerated until a desired residual contaminant level is reached, and then the supernatant water is usually recycled and the slurry is discharged. Due to the ongoing aeration in these systems, many volatile organic substances are not biodegraded but rather are air-stripped. Some systems treat these air-stripped volatiles in a carbon adsorption filter whereas other systems simply discharge them to the atmosphere.

A fourth system, known as the EIMCO Biolift® system, utilizes a bioreactor that is a tank having a bottom, upstanding walls fixedly mounted thereon and a sealed top or cover, and which is adapted to receive and contain a slurry. The tank is fitted with a mechanical mixing means that operates to effectuate agitation and suspension of the solid particles within the slurry housed within the tank. An air supply operates to provide oxygen, which is a necessary component of the biooxidation reaction taking place within the bioreactor. The air supply also is configured to provide suspension of the particulate within the slurry liquid housed within the tank. In addition, an air lift is provided for recirculating particulate which may have settled out of the slurry. The Biolift® system may be operated in continuous mode by using a screening device and exit conduit located near the top inside the tank to draw off treated water and excess particulate matter.

Considerable literature is available describing slurry reactors for municipal and farm sewage digestion, but the total solids for these applications are usually below 10 wt %. The density of sewage sludges is much closer to the density of water than is the density of soil, and therefore the mixing method and design of these sewage sludge stirred reactors can be significantly different than that of soil-slurry reactors. Many sewage digester designs are unstirred, and the predominant mixing mechanism is the $CO_2$ and $CH_4$ gas generated in the reactor. The mixing occurs as these gas bubbles rise through the slurry. Propeller type mixers are sometimes added for more thorough mixing and to try to maintain the solids in suspension. The current design of most soil-slurry reactors is to finely pulverize the material and try to keep it in suspension with significant power input to shaft stirrers, aerators, recirculation pumps or a combination of these methods. The alternative approach is to not mix at all or to mix only occasionally. With the extended residence time required for most biodegradation, there is probably no need for a high shear or complete suspension agitation, especially for an anaerobic design.

In aerobic soil-slurry reactors it is difficult to maintain high oxygen concentrations due to the tendency for gas bubbles to coalesce. Also, since the reactors are usually low in profile, there is a very short liquid-gas contact time and a small surface area to volume ratio of the bubbles. Mechanical agitation is usually required to disperse gas bubbles and give smaller gas bubbles, but as the solids concentration increases the agitation effect decreases.

Common to all hazardous waste treatment systems utilizing microorganism activity is the requirement of providing an adequate supply of nutrients to the microorganisms. This provision allows biomass growth and facilitates the occurrence of biochemical reactions. Various approaches have been used to optimize bioactivity level in reactor vessels. In those systems wherein a multiplicity of connected reactor vessels have been suggested, e.g. cascade systems, a common problem is the retention and maintenance of biomass in a given reactor as effluent from the reactor is directed to the next reactor.

The clean-up of hazardous waste sites requires innovative approaches that are cost effective. Biological systems can play an important role in soil bioremediation, as they have in the field of wastewater treatment. In order to be cost effective in contaminated soil treatment, however, bioreactor vessels and processes are needed that can handle high solids concentrations and large throughput volumes with a minimum of input and/or operating energy.

3. Related Art—Wastewater Remediation

Dissolved organic matter and suspended solids are often removed from wastewaters by a combination of biodegradation and filtration. Conventional designs for microbial water treatment processes are based on suspended microorganisms to degrade organic matter in wastewaters. These activated sludge processes are in wide usage, but they are not efficient in removing waste materials, and they require large facilities. Attached-growth systems, with bioreactors packed with inert media on which microorganisms can attach and grow, are much more efficient than suspended growth systems.

A variety of arrangements have been used to clean wastewaters using biological treatment and filtration. One arrangement has been bioreactors in line with sedimentation tanks and filters. The reactor can be as simple as a tank where air is injected and aerobic bacteria are grown on inert carriers such as plastics and sand. U.S. Pat. No. 5,007,620 discloses a bioreactor equipped with a sweeping means adapted for sweeping and scouring the bottom of the bioreactor. Stationary diffusers are used to aerate the bioreactor. By these means, an aerated slurry can be maintained by means of mechanical agitation and aeration.

Alternatively, a bioreactor can be operated anaerobically in processes such as anaerobic digestion and denitrification. U.S. Pat. No. 3,970,555 discloses a method for backwashing a filter by injecting a fluid, such as air or water, to dislodge gas bubbles trapped in a filter bed. Such backwashing also removes solids clogging the filter bed.

Bioreactors operated with inert media for supporting microbial growth, are termed "biofilters", and have been operated with a stationary filter medium or a movable filter medium. The filter medium typically consists of plastic materials or inorganic materials such as sand. Stationary filter media must be periodically cleaned by a reversed-flow washing, termed "backwashing". Backwashing, especially when done with injected water and air, can effectively clean the medium. However, the backwash fluids must be collected and treated. Also, the biofilter must be periodically removed from service in order to do the backwashing.

Fluidized bioreactors have been developed for continuous operation without backwashing (U.S. Pat. No. 5,007,620). However, such bioreactors require continuous agitation with high energy consumption. In addition, fluidized bioreactors cannot clean wastewater by filtration.

SUMMARY OF THE INVENTION

The instant invention is a slurry mixer/contactor for a slurry, suspension or settled bed reactor system. The mixer/contactor is particularly well-suited for the biological remediation of liquid waste streams or contaminated sludges or soils. The reactor system having the mixer/contactor of this invention may operate with microorganisms living in the reactor aerobically or anaerobically. Also, the reactor system may operate with microorganisms in the reactor using oxidative or reductive pathways to biodegrade contaminants. To further increase activity in the bioreactor, additional ingredients, including solids, liquids or gases, may be added to the slurry, suspension or settled bed in the reactor.

The reactor having the mixer/contactor in one embodiment is an upright generally cylindrical vessel with a flat bottom and a covered top. In the inside of the vessel, preferably along the cylinder centerline, is a vertical conduit, also called a supply conduit, extending from near the top to near the bottom. At the bottom of the vertical conduit is the inlet to at least one generally horizontal, stirrer blade in fluid connection with the vertical conduit. The stirrer blade has outlet openings in it or on it so fluid may pass there-through. The stirrer blade may rotate around the vertical conduit if the conduit is fixed, or the conduit, with the stirrer blade fixed to it, may rotate around in the vessel. In any event, the rotation of the stirrer blade is caused or made easier by the hydraulic forces of fluid flowing out from the stirrer blade. This rotation may be caused or made easier by a fluidization effect, by a jet propulsion effect, or both. This way, rotation of the stirrer blade may be created or eased near the bottom of the vessel, enhancing mixing of the microorganisms with the sludge or soil in the slurry, suspension or settled bed in the vessel, without unnecessarily damaging the microorganisms and without having to fluidize the complete vessel contents. Also, this way liquid and/or slurry from near the top of the reactor may be re-distributed into the sediment near the bottom of the reactor for fresh re-contact and further desorption and reaction of contaminants from the sediment to permit further biodegradation.

In a preferred embodiment, the bioreactor vessel has a water recycle outlet port and a gas recycle outlet port. At the water recycle outlet port, which is below the fill line for the reactor, is a water recycle outlet conduit leading to the inlet of a water recycle pump. The pump delivers recycled water back to the bioreactor vessel through a water inlet conduit connected to the vessel at a water recycle inlet port. Preferably, the water inlet port is connected to the vertical conduit in the center of the vessel, and the flow of recycled water helps to provide the hydraulic forces for fluidizing the sediment in the immediate vicinity of the blade and/or the jet propulsion that results in rotation of the stirrer blade.

At the gas recycle outlet port of the bioreactor vessel is a gas recycle outlet conduit leading to the inlet of a gas recycle pump or compressor. The compressor may deliver recycled gas and/or fresh gas to the bioreactor vessel through a gas inlet conduit connected to the vessel at a gas inlet port, or connected to the water inlet conduit. This way, water and gas from the bioreactor vessel may be recycled and provided to the vertical conduit to help create rotation of the stirrer blade, and better mixing and contacting of the slurry or suspension and the microorganisms in the bioreactor vessel.

Preferably, the mixer/contactor is one, generally horizontal blade in fluid connection with the vertical conduit. The blade has outlet openings at or near its leading edge so that fluid passing through the vertical conduit and to the blade may pass from the blade through the openings. This way, a fluidization zone is created in the slurry, suspension or settled bed of solid particles, in the region of the openings at or near the leading edge of the blade. By "leading edge" of the blade is meant the front edge or side of the blade relative to the direction of rotation of the blade. By "trailing edge" is meant the back edge or side of the blade relative to rotation. More than one blade may be used, and blades at various depths in the reactor may also be used. When a plurality of blades is used, they may rotate independently of, or together as a unit with, the other blade(s).

The fluidization zone created by the flow of fluid from the outlet openings in the blade has less density than the rest of the slurry, suspension or settled bed throughout the reactor. Therefore, any generally horizontal force on the blade will tend to cause it to rotate into the fluidization zone. This horizontal force on the blade may be created by a propulsion jet at the trailing edge of the blade. Or, this horizontal force may be created by the horizontal component of the weight vector from settling sediment on a rear, downwardly sloping portion of the blade as the sediment descends from a fluidized state to a settled state at the trailing edge of the blade. Or, this horizontal force may be created by the input from an external power source, like an electric motor, for example, connected to and rotating the vessel's vertical conduit. Therefore, the blade rotates, or its rotation in the reactor vessel is made easier, due to the hydraulic forces of fluid flowing out from the stirrer blade.

This invention also relates to the use of a single bioreactor to achieve both biological degradation and the filtration of suspended solids. The mixing/contacting blade intermittently suspends the filtration medium as the blade rotates through the medium to efficiently backwash and clean it.

One objective of this invention is to provide an efficient biofilter equipped with a filter bed through which movable blades can be propelled by the injection of fluids, such as air and water. Thereby, the filter bed can be intermittently suspended and efficiently cleaned of trapped solids and gases. Another objective is to provide a biofilter capable of both microbial degradation of wastewater contaminants and contaminant removal by filtration.

DETAILED DESCRIPTION OF THE PREFERRED EMBODIMENTS

Figure 1:
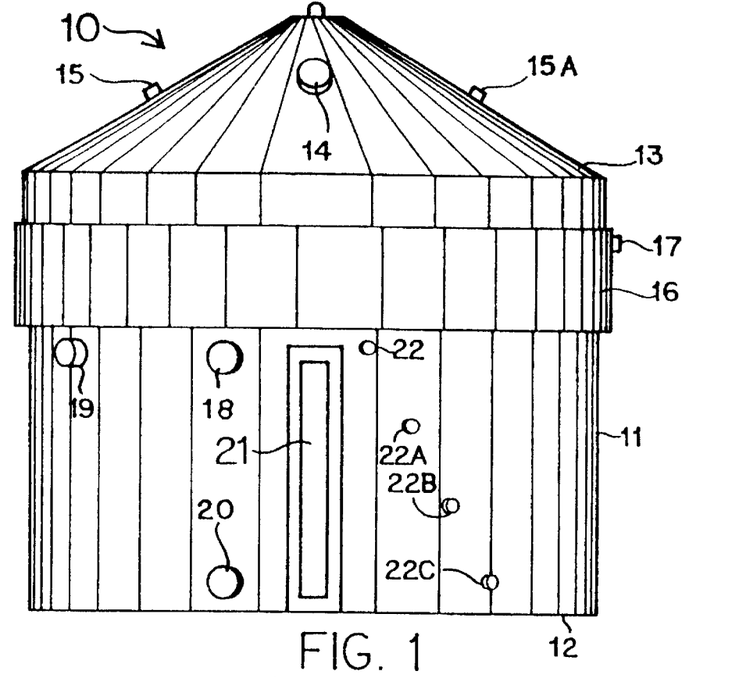
FIG. 1 is a partial side view of one embodiment of the reactor of this invention.

Referring to the Figures, there are shown several, but not the only, embodiments of the reactor 10 having the mixer/contactor blade of this invention. Referring to FIG. 1, reactor 10 is an upright, generally cylindrical vessel 11 with a flat bottom 12 and a conical top 13. In conical top 13 is optional fill port 14 and gas recycle outlet ports 15 and 15(A). Conical top 13 fits within annular water seal 16, which has water seal overflow port 17. In the side wall of cylindrical vessel 11 are water recycle outlet port 18, water recycle inlet port 19, drain port 20, viewing window 21, and sample ports 22, 22A, 22B, and 22C.

Figure 2:
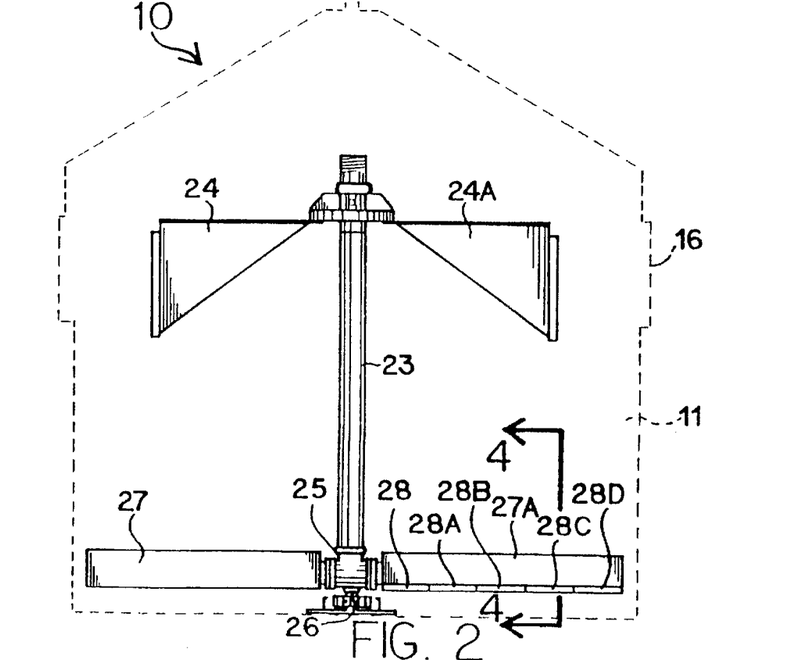
FIG. 2 is a schematic, cross-sectional view of the reactor depicted in FIG. 1, showing some of the reactor's internal structure.

Referring to FIG. 2, reactor 10 has water seal 16 and a vertical conduit 23 supported along the centerline of vessel 11 by bracing 24 and 24A. Vertical conduit 23 terminates near the bottom 12 of vessel 11 at "T" fluid connection 25. "T" connection 25 is rotatably supported on bottom 12 by spindle bearing 26. At the horizontal termini of "T" connection 25 are hollow stirrer blades 27 and 27A. The blades 27 and 27A are in fluid connection with vertical conduit 23, and have in them openings 28, 28A, 28B, 28C, and 28D.

Figure 3:
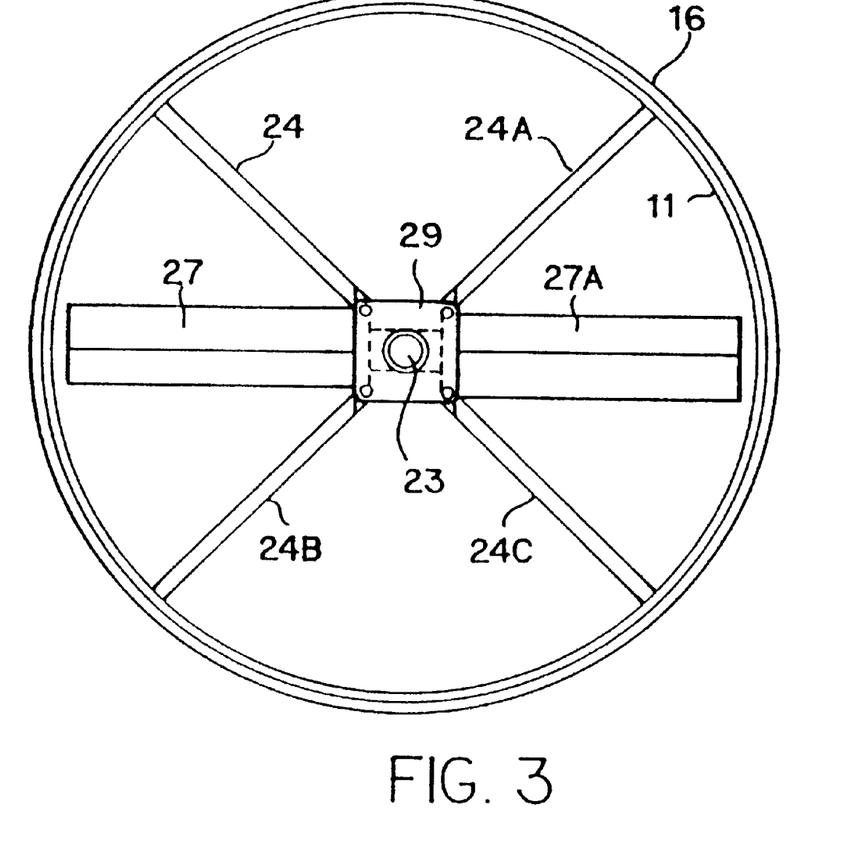
FIG. 3 is a schematic, top cross-sectional view of the reactor depicted in FIGS. 1 and 2.

Referring to FIG. 3, reactor 10 has cylindrical vessel 11 with water seal 16, and bracing 24, 24A, 24B, and 24C for supporting vertical conduit 23. At the bottom end of vertical conduit 23 are horizontal stirrer blades 27 and 27A. In this pictured embodiment, vertical conduit 23 rotates, and it is rotatably supported near its top in the bracing by hub bearing 29.

Figure 4:
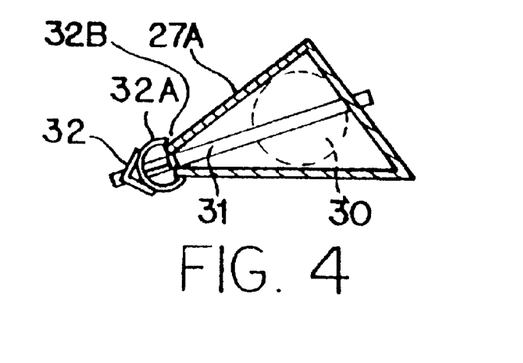
FIG. 4 is a cross-sectional side view of the mixer/contactor blade of the invention, from the line 4—4 in FIG. 2.

Referring to FIG. 4, stirrer blade 27A has a generally triangular cross-sectional shape. The circular "T" connection 25 inlet to the blade 27A is indicated at 30. At several locations along the length of the blade 27A, bolts 31 with leading edge retainers 32 and 32A are provided to stiffen and stabilize blade 27A. A fluid flow path or gap 32B is provided at several locations along the leading length of the blade 27A between it and edge retainer 32A. This way, fluid can exit the blade 27A at gaps 32B and fluidize the sediment bed, and propel the blade around in the reactor.

Figure 5:
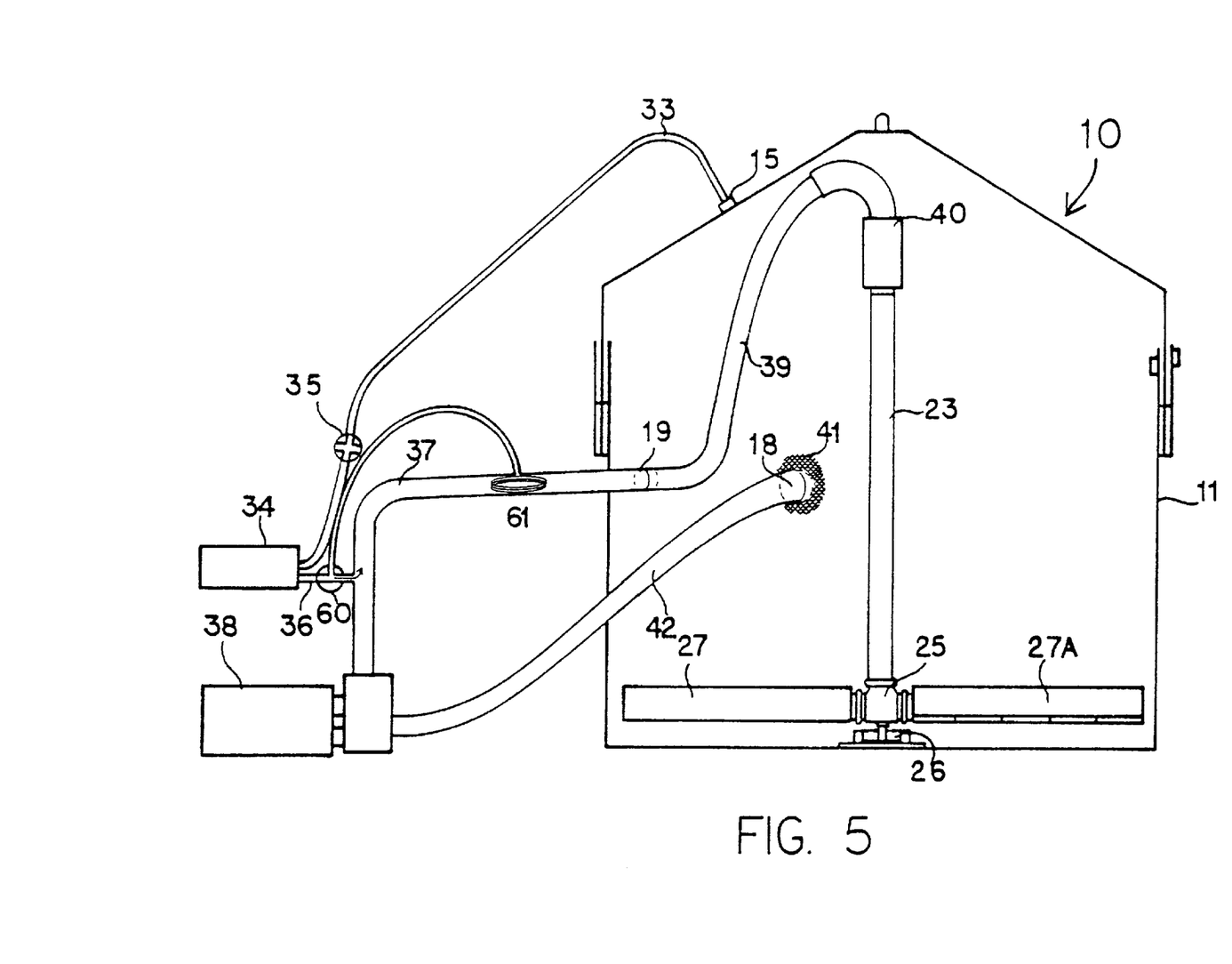
FIG. 5 is a schematic, cross-sectional view of the reactor depicted in FIGS. 1–4, showing the reactor's additional external equipment.

Referring to FIG. 5, reactor 10 has gas recycle outlet port 15 and gas recycle outlet conduit 33 leading to air pump or compressor 34. In recycle outlet conduit 33 is optional 4-way gas valve 35. Air pump 34 discharges compressed recycle gas into gas inlet conduit 36, which is connected and discharges into water recycle inlet conduit 37. Recycle inlet conduit 37 is connected on its first end to water pump 38, and on its second end to water recycle inlet port 19. Inside vessel 11, interior conduit 39 is connected on its first end to inlet port 19, and on its second end to the first end of rotating swivel connection 40. Swivel connection 40 is supported by hub 29 as shown in FIG. 3, and connected on its second end to vertical conduit 23. Swivel connection 40 permits interior conduit 39 to be fixably connected to inlet port 19 and swivel connection 40, and, at the same time, permits vertical conduit 23 to be rotatably connected to swivel connection 40. This way, vertical conduit 23, "T" connection 25 and stirrer blades 27 and 27A may rotate inside vessel 11.

During operation, the slurry or suspension inside vessel 11 is maintained above the level of water recycle outlet port 18. Recycle outlet port 18 is equipped on the inside of vessel 11 with an outlet screen 41. Screen 41 prevents the solid particles in the slurry or suspension greater than the size of the screen openings from exiting the vessel 11. Water recycle, however, is permitted to exit outlet port 18, and travels via water recycle outlet conduit 42 to the inlet of water pump 38. The discharge of water pump 38 travels via inlet conduit 37, inlet port 19, interior conduit 39, swivel connection 40, vertical conduit 23, "T" connection 25, "T" connection inlet 30, and stirrer blades 27 or 27A back into the interior of vessel 11 near its bottom. This way, the hydraulic forces of the water recycle rotates, or makes easier the rotation of stirrer blades 27 and 27A, enhancing mixing of the microorganisms with the sludge or settled sediment near the bottom of vessel 11 without unnecessarily damaging the microorganisms. This way, the reactor may be operated with, for example, soil slurries at greater than 50 wt % total solids.

Preferably, the bioreactor has four basic modes of operation. In these four modes, the water and air pumps are controlled by a repeat cycle timer that allows either or both pumps to be operated intermittently or continuously.

First Mode. In the first mode of operation, water is recirculated through the blade which fluidizes the slurry, suspension or settled bed in front of the blade and propels the stirrer through the slurry, bringing fresh liquid in contact with the soil for rapid mixing. The water exiting the nozzle propels the stirrer and also brings solids up into suspension from the bottom and rapidly mixes them. If the circulation is for a short time, the solids are mixed but not so much that they are fully suspended and sucked into the recycle outlet.

Second Mode. In the second mode of operation, the air pump can be added to the operation, allowing very efficient aeration for aerobic reactions, and increasing vertical mixing with the rising bubbles. Since the water and air are both under pressure, the amount of oxygen dissolved in the water can be increased considerably above saturation at atmospheric pressure. For high biological oxygen demand (BOD) systems, this will allow significantly higher oxygen mass transfer rates than for a normally bubbled and stirred reactor. If foaming is a problem with a specific slurry or suspension, the addition of air can be intermittent, with the foam subsiding when air is not being added.

One way to add air to the operation is to provide a bubbleless oxygenation tube at the discharge of the air pump or compressor 34. For example, with three-way valve 60 in gas inlet conduit 36 and with bubbleless oxygenator 61 in recycle inlet conduit 37, air under pressure is routed through oxygenator 61 into reactor 11. This way, foaming in reactor 11 may be minimized. Bubbleless oxygenator tubes are available from, for example, Membran Corporation, Minneapolis, Minn., U.S.A.

Third Mode. In the third mode of operation, the air pump will pump headspace gases as recycle gases into the water recycle flow, thereby increasing the mixing rates and allowing more complete degradation of volatile compounds in the slurry. This will also increase vertical mixing in anaerobic operations and reintroduce volatiles into the slurry for further degradation.

Fourth Mode. The fourth mode of operation is a combination of the above modes; the modes can be operated on an intermittent basis to reduce operational costs or to maintain microaerophilic conditions. Also, by switching between the second and third modes with the 4-way valve 35, there will be no excess aeration or volatiles lost. This system can be easily interfaced with a computer for active control of the operating mode.

The reactor has the additional benefits of being an intermittently cleaned sand filter with very high biomass retention. In fact, the bioreactor may be used as an intermittently backwashed sand filter without substantial biodegradation. This allows for very efficient space utilization and exceptionally low effluent BOD and suspended solids concentration for a single-pass aerobic or anaerobic reactor. This system can also operate as a sequencing batch reactor, and/or as a mixed mode reactor with both aerobic and anaerobic operations.

For continuous operations, fresh wastewater or soil slurry may be added to the water recycle outlet conduit 42, and excess treated water removed from drain port 20 at the bottom of the reactor. This may be done without significant loss of the sand or the biomass from the interior of the reactor if a suitable screen is used inside drain port 20. Depending on the source of fresh waste-water, it may be supplied directly to the blade through vertical conduit 23, and not through the recycle pump.

This novel slurry reactor is an intermittently mixed reactor that has the capability of intermittently fluidizing over 50% wt/wt sand with complete mixing occurring every minute in a 200 gallon pilot-scale reactor. The sand in the reactor can also be operated very efficiently as an anaerobic expended bed bioreactor with intermittent mixing (<5% of the time) and still have very complete and thorough mixing. High biomass retention allows for an old sludge age and very high degradation rates. In addition to providing for an attachment surface for the retention of biomass, the sand layer acts as sand filter as the water is removed from the bottom of the reactor. Any suspended material, including biomass, is retained by the sand filter therefore allowing very high biomass densities to be maintained, with resulting very high activity. As the mixing blade moves through the sand bed it fluidizes the sand near the blade and keeps the biomass from plugging the sand or the screened outlet. The flocculent biomass goes into suspension and is fluidized, while the attached biomass has fresh liquid brought into contact with the biofilm. This enables a very high rate of degradation in a small volume. The backwashing cycle may be controlled by monitoring the pressure drop across the settled bed or the flow rate out of the drain port. A pressure drop above the set-point, or a flow rate below the set-point, would initiate the backwash cycle.

When biomass wasting is desired or required, the reactor can be fully fluidized and the recycle can be directed to a suitable container for a settling basin. An alternate wasting method is to drain some of the liquid away before directing the recycle to a suitable settling basin. This wasting cycle can be incorporated into a weekly operation, or it could possibly be an automatic part of the normal cycling of the reactor. The intermittent mixing of only about 5% of the time consumes very little energy, but has significant advantages in both the operation and efficiency of the degradation. The range of wastewater strengths as influent can vary from about 300 to greater than 30,000 mg/l COD depending on the final design of the system.

An embodiment could also include more than one reactor in series or parallel with effluent from either below the sand level or from above the sand level from the first reactor (which would likely be operating in an anaerobic mode) to a second reactor which could be operating aerobically and the effluent from the second reactor could be moved from below the sand level for very good effluent quality. By having the second reactor actually be two reactors in parallel, then these two reactors could operate in alternating batch mode which would enable effluent to be drawn from one of the two reactors that had just completed a settling mode. This embodiment would not require the removal of the water from below the sand but it would not preclude it either. One of the series of reactors could be setup for a denitrification process as is well known in the industry.

Additionally, by having one of the reactors operating with an aerobic slurry phase and a blade in the upper layer of the sand to fluidize and clean only the upper region of sand, the lower region of sand could be anaerobic for denitrification to occur. Swivels of some companies allow two or more isolated flows to occur so the liquid from the aerobic region would only fluidize the upper sand and liquid from the anaerobic portion could be used to fluidize the lower portion. An alternate method to have two different redox states in the sand regions is to have a two speed pump or other flow control means on the recycle flow so that at a low flow only the upper sand is fluidized but at higher flow rates the complete bed is mixed.

There are also times that the influent water flow will be great enough that a recycle pump is not necessary and the influent flow can go through the blade and nozzles to fluidize the reactor contents and sand bed if a sand bed is part of the system.

Figure 6:
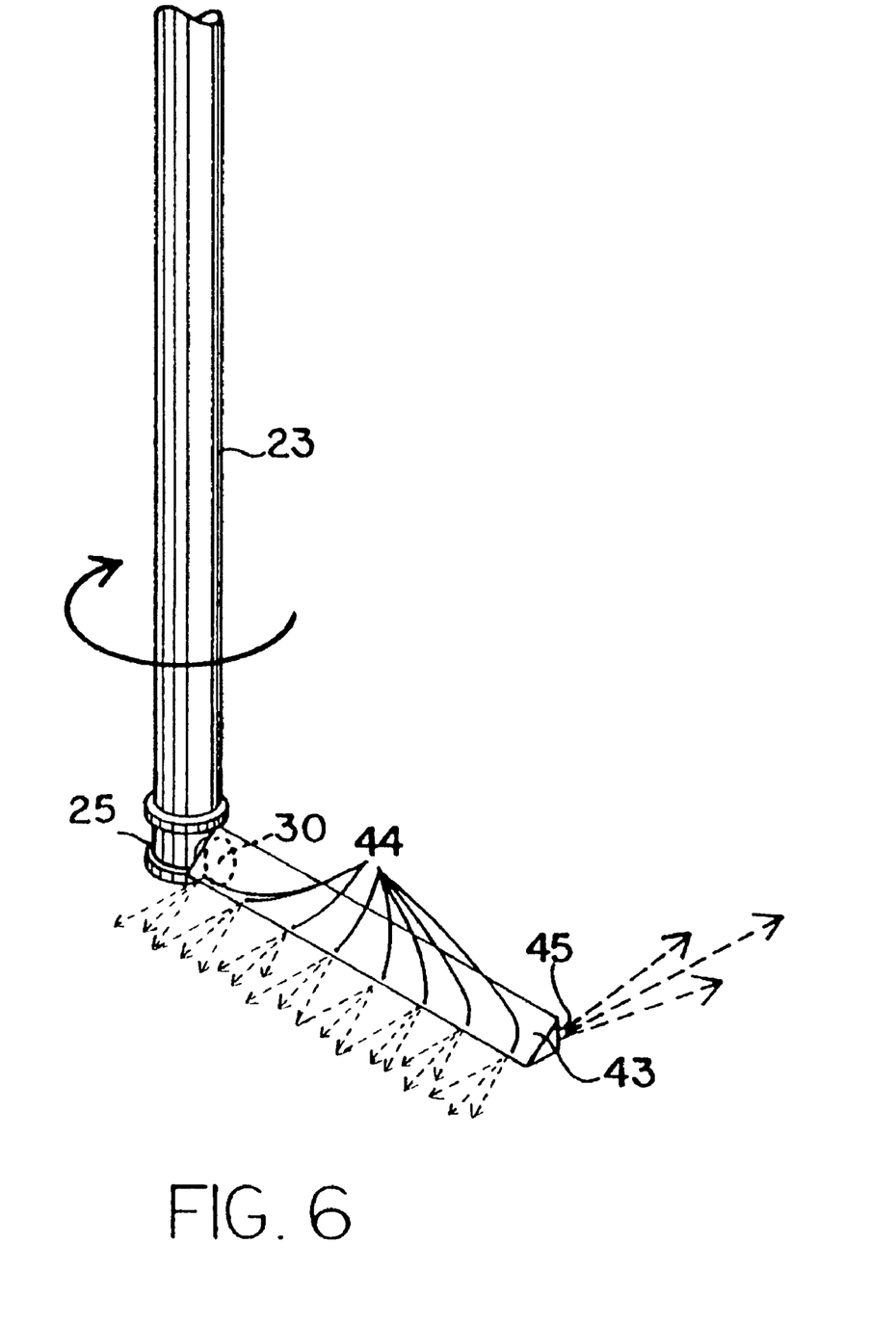
FIG. 6 is a schematic, partial detail isometric view of one embodiment of the mixer/contactor blade of the invention, showing the fluid flow lines out from it during operation.

Referring to FIG. 6, triangular stirrer blade 43 has fluidization openings 44 in its front, or leading, side, and jet propulsion opening 45 in its back, or trailing, side. When fluid is directed into blade 43 from vertical conduit 23, "T" connector 25 and "T" connector inlet 30, the fluid flows out from fluidization openings 44 and jet propulsion opening 45.

Figure 7:
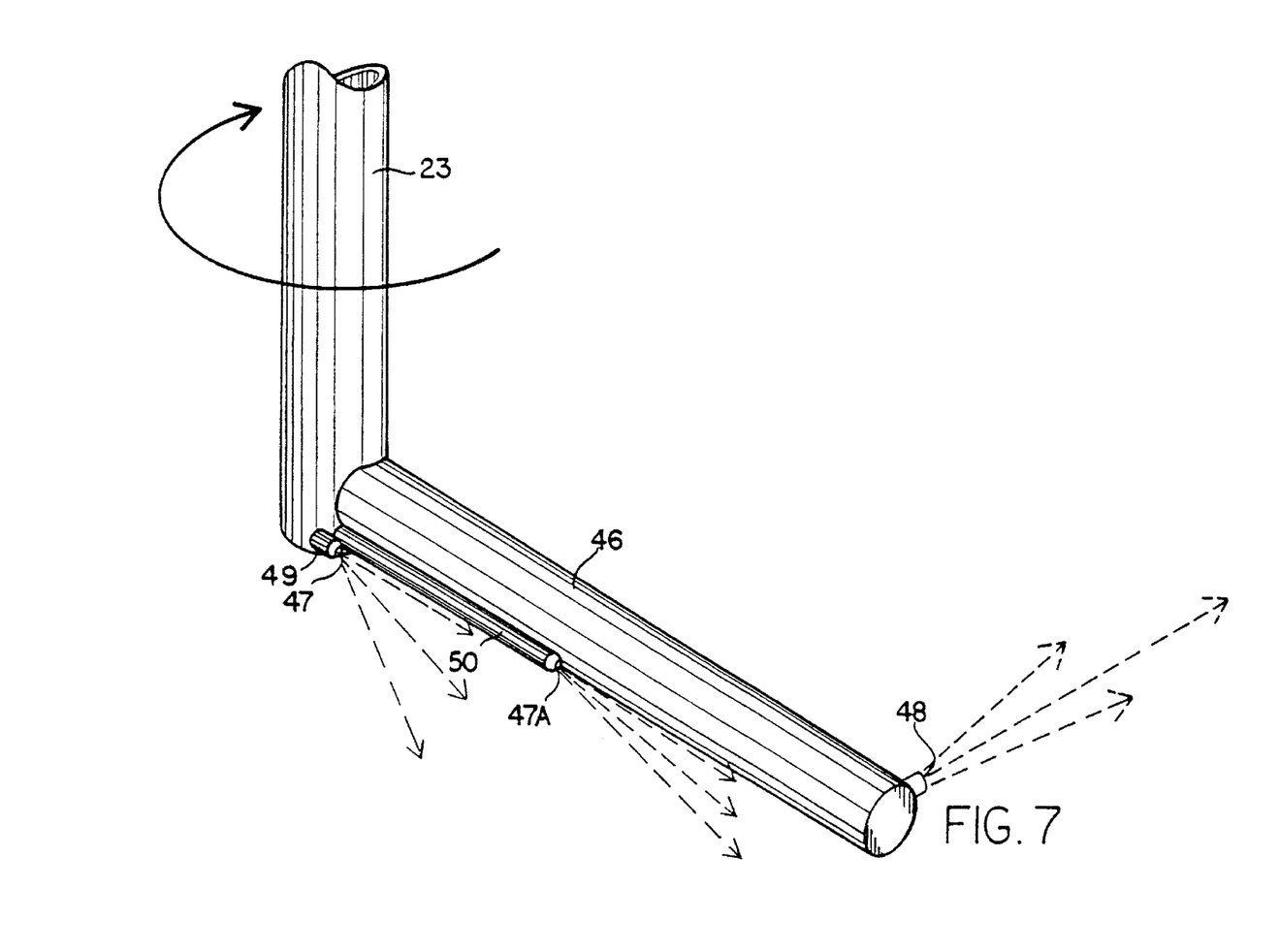
FIG. 7 is a view as in FIG. 6, but of another embodiment of the mixer/contactor blade.

Referring to FIG. 7, round stirrer blade 46 has fluidization openings 47 and 47A which are the outlets of relatively short conduits welded parallel to the leading edge of blade 46. The conduit 49 is very short and its opening 47 is near vertical conduit 23. The conduit 50 is longer and its opening 47A is near the middle of stirrer blade 46. Both openings 47 and 47A are pointed parallel to the leading edge of blade 46. This way, the fluidization zone created by fluid flowing out of openings 47 and 47A is at or near the leading edge of blade 46. Also, round stirrer blade 46 has jet propulsion opening 48 in its back, or trailing, side.

Figure 8:
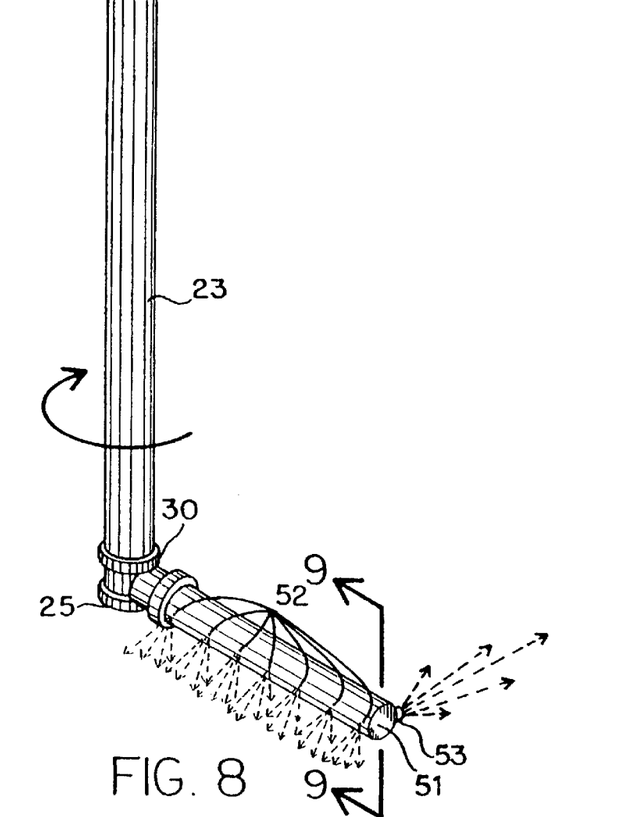
FIG. 8 is a view as in FIGS. 6 and 7, but of yet another embodiment of the mixer/contactor blade.

Referring to FIG. 8, round stirrer blade 51 has fluidization openings 52 in its front side, and jet propulsion opening 53 in its back side. When fluid is directed into blade 51 from vertical conduit 23, "T" connector 25 and "T" connector inlet 30, the fluid flows out from fluidization openings 52 and jet propulsion opening 53.

Figure 9:
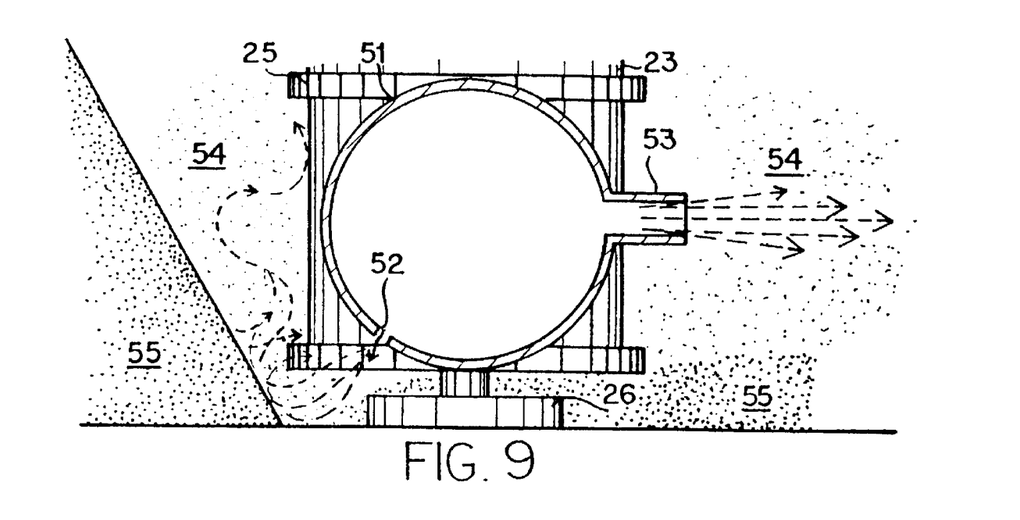
FIG. 9 is a partial, cross-sectional side view from line 9—9 of the mixer/contactor blade depicted in FIG. 8, showing the fluidization effect and the propulsion effect in the settled bed around the blade.

Referring to FIG. 9, the outflow of fluid from fluidization openings 52 in stirrer blade 51 creates a zone 54 of fluidized sediment in the region in front of blade 51 near the openings 52. Zone 54 has relatively less density than non-fluidized zone 55 that exists behind blade 51 and elsewhere in the sediment throughout the reactor. Therefore, the tendency is for blade 51 to rotate in the direction of fluidized zone 54 whenever any rotational force is exerted on blade 51, that is, in the direction of the arrow in FIGS. 6–8. This way, blade 51 rotates around the bottom of reactor 10, fluidizing a relatively small segment of the sediment bed before it as it rotates. Also this way, the solid particles that make up the sediment bed are periodically mixed and recontacted with fresh feed or recycle flowing out from openings 52, enhancing desorption of contaminants from them, and biodegradation.

FIGS. 4, 6–9 illustrate stirrer blades that comprise an elongated member which is generally hollow and that have fluid outlet openings at or near their leading sides. FIGS. 4, 6, 8 and 9 illustrate stirrer blades in which the leading side outlet openings comprise apertures located in the main, elongated hollow stirring member. FIG. 7, on the other hand, illustrates a stirrer blade with a leading side comprising horizontal conduit members, attached to the main member, for the outlet openings. Especially in embodiments such as FIG. 7, in which the outlet fluid path is through conduits or other hollow apparatus rather than apertures in the main member, the main, elongated stirring member optionally may be solid rather than hollow, especially if no trailing side jet is desired.

Figure 10:
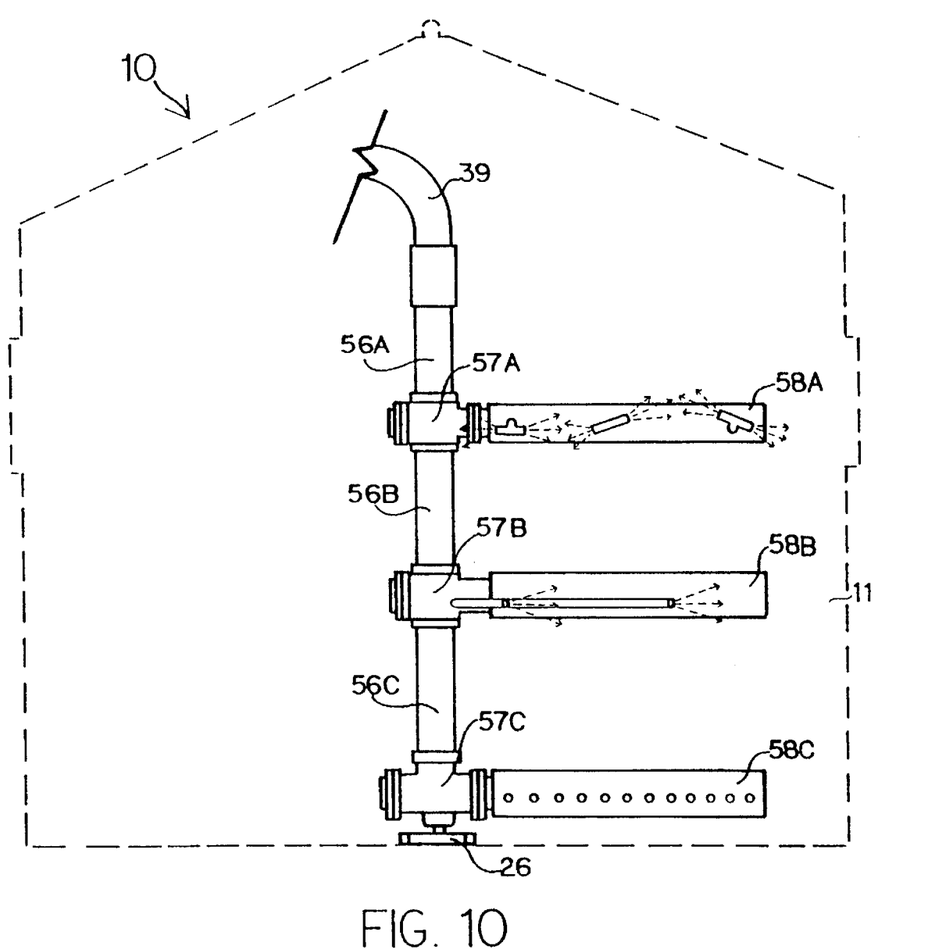
FIG. 10 is a schematic, partial side view of another embodiment of the invention with a plurality of mixer/contactor blades at different depths in the reactor.

Referring to FIG. 10, reactor 10 has several vertical conduits 56A, 56B and 56C, and several rotary unions 57A, 57B and 57C connecting the vertical conduits. Each rotary union has a horizontally-extending hollow stirrer blade, 58A, 58B and 58C, respectively. Interior conduit 39 is connected to the top of rotary union 57A. The bottom of rotary union 57C is rotatably supported by spindle bearing 26. The blades 58A, 58B and 58C are in fluid connection with the respective rotary unions 57A, 57B and 57C, which in turn are in fluid connection with the respective vertical conduits 56A, 56B and 56C. Depending on the type of rotary union selected, blades 58A, 58B, and 58C may rotate independently of one another, in mixed combination of independent or dependent rotation, or all together as a unit. This way, the blades may rotate in the settled bed at one speed, and in the slurry or suspension above the settled bed at a different speed. In blade 58A it can be seen that small "T" fittings may be added to the fluid outlet openings to better control the direction of fluid flow from the openings. The T-fittings may be at −45 to +45 degrees from parallel to the blade.

Figure 11A:
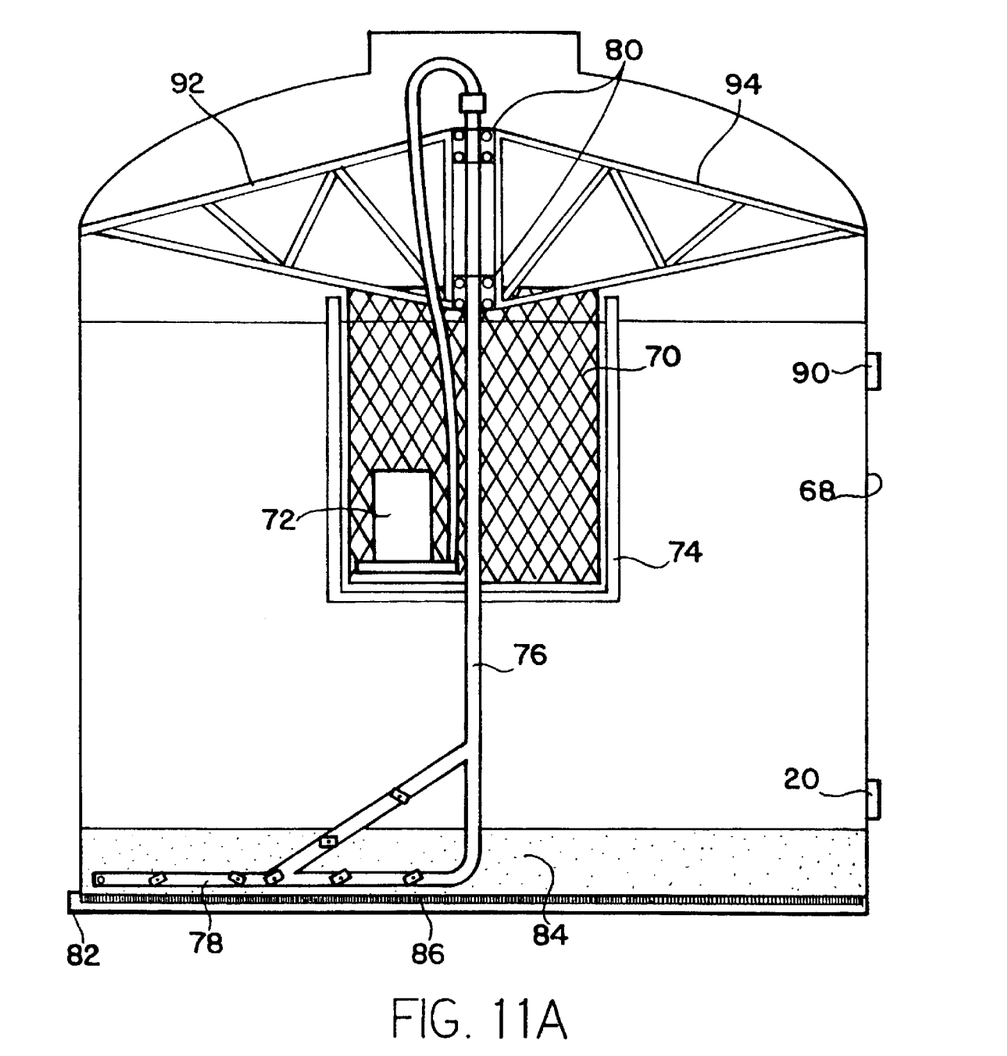
FIG. 11A is a schematic, side cross-sectional view of another embodiment of a reactor of the invention with a submersible pump in it.
Figure 11B:
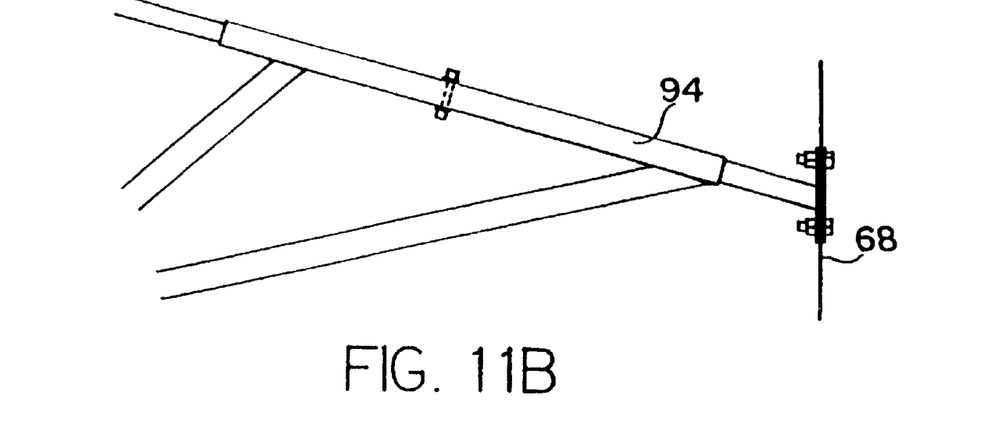
FIGS. 11B and 11C are schematic detail side and top views, respectively, of reactor internals for the embodiment of FIG. 11A.
Figure 11C:
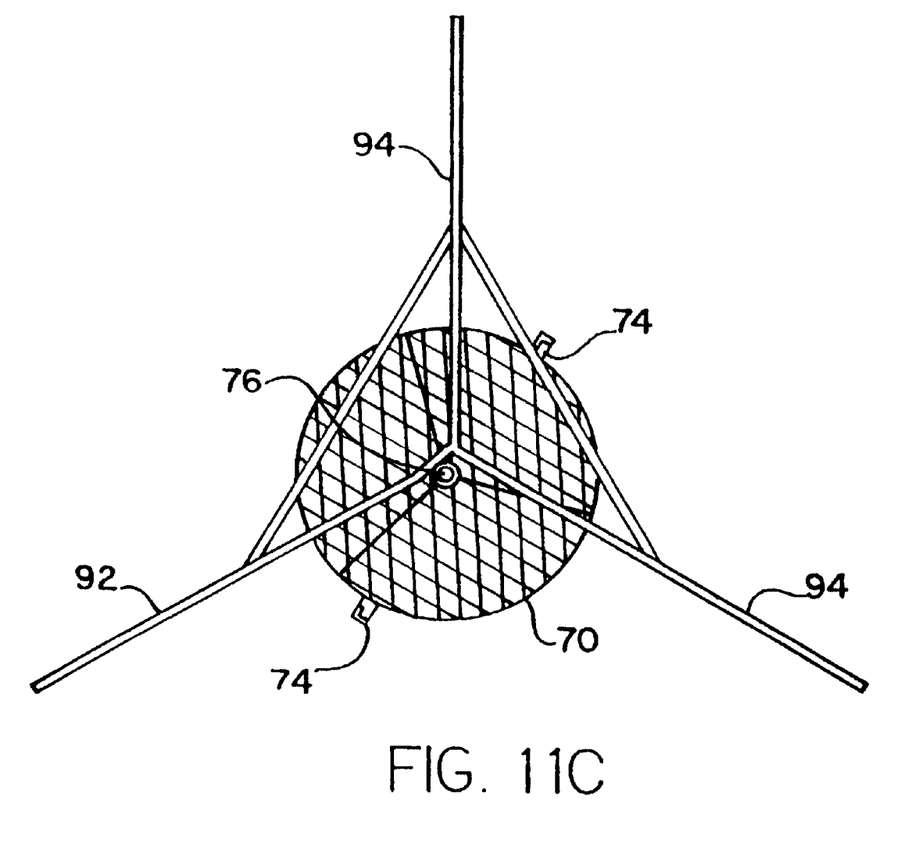

Referring to FIGS. 11A, 11B, and 11C, they show another scheme for mounting the blade assembly inside an inexpensive tank 68 (i.e., polyethylene 8–12 ft. diameter, by 8–14 ft. high). The center hatched area is a cylindrical, screen 70 region in which may be located a submersible pump 72. A wiper/scraper/brush 74 may be mounted on the central conduit 76 for rotating around with the blade 78 to clean the screen 70. The pillow block bearing 80 (with split halves) may be both above the water level for accessibility and ease in removing the blade 78 if needed and for trouble free service. The lower, left outlet pipe 82 is for removing water as filtered water, from below the sand bed 84 through the slotted screen (available from Cook Screen Company and others). The lower right pipe 20 could be for water coming into the reactor and also for wasting solids (but not the sand) by stopping the mixing and allowing solids to settle and then opening or pumping out of that port. The upper right pipe 90 could be a fill port or an overflow port if it were higher. The top view shows the upper two truss braces 92, 94 are welded together with the lower one bolted to it after inserting everything into the tank through the 3 foot diameter access port. The cycle time may be timer-controlled, for example, or it may be controlled by the pressure drop across the sand bed 84, or it may be controlled by a flow control valve on the outlet pipe from the lower pipe (drain port) 20. By having a pump on the outlet pipe 82, a much higher flow rate could pass through the sand bed 84 and the reactor would operate more as a filter and as a bioreactor with a very short retention time.

The stirrer or mixer/contactor blade of this invention, then, may be practiced in several embodiments. The size and shape of the blade may be varied, as long as outlet openings may be placed at or near its leading edge, and as long as the trailing side of the blade is dissimilar from the leading side. The trailing side may be dissimilar from the leading side in that the number and/or type of fluid outlet openings are different from those of the leading side. For example, the trailing side may have one fluid outlet while the leading side has a plurality of outlets, as shown in FIG. 7. Or, the trailing side may have no fluid outlets, while the leading side does have outlets. Also, the trailing side may be dissimilar from the leading side in its shape or profile. Preferably, the blade has a shape which encourages sediment settling on it to be directed towards the trailing edge of the blade as the sediment continues to descend. With such a shape, the horizontal component of the weight vector from the settling sediment pushes the blade forward into the fluidization zone at the front of the blade. For example, the blade may be shaped to have a side profile similar in general shape to an airplane wing. When the blade is shaped appropriately, adequate forward horizontal force is supplied by the settling sediment, making optional the propulsion jet opening(s) at the trailing edge of the blade.

So, the selection or design of a particular blade for use in the invention depends upon many factors, including: the type of liquid and the size and density distributions of the solid particles; the rate of the biodegradation reactions, etc. Therefore, a preferred blade design depends upon many factors like these.

It is also apparent that adding a motorized device to assure rotation of the blade would fall within the scope of this invention. One main aspect of this invention is to provide energy to fluidize material in the immediate vicinity of the blade and then move this fluidized zone around the complete reactor. Whether or not the rotational force comes solely from the hydraulic forces or also from a mechanical torque provider is also within the scope of this invention. In many embodiments of the invention, a motorized drive means is not needed to power the blade(s). Optionally, a motor, or other braking means may be added to slow, or otherwise control the speed of the rotating blade(s).

It is also apparent that this described reactor and process is suitable for high efficiency mixing of a very wide variety of materials with low energy requirements, including gas, liquid or solid or any combination thereof, for a wide variety of processes, including physical, biological, catalytic or chemical processes.

Although this invention has been described above with reference to particular means, materials and embodiments, it is to be understood that the invention is not limited to these disclosed particulars, but extends instead to all equivalents within the scope of the following claims.

What is claimed is:

1. A process for treating a contaminated soil, sludge, or slurry, the process comprising:
   providing a sludge or slurry containing solid particles in a reactor;
   maintaining a suspension or slurry of the solid particles simultaneously with a substantially settled bed of the solid particles in the reactor;
   wherein maintaining the suspension or slurry is done with a minimum energy input by rotating a generally horizontal stirrer blade within said reactor, the blade having a certain direction of rotation, a leading side, and a trailing side, and openings, wherein the openings comprise an opening at or near the leading side and an opening at or near the trailing side, wherein said rotation is powered by fluid flowing out of said opening at or near the leading side to create a fluidized zone in front of the blade and through said opening at or near the trailing side to propel the blade and thereby causing the blade to move forward;
   the process further comprising:
      filtering and then removing liquid from the reactor by passing the liquid down through a filter bed, which is the substantially settled bed of solid particles, so that the filtered liquid has less suspended solids than the liquid in the reactor above the settled bed, and causing the filtered liquid to exit the reactor through a screened outlet that substantially retains the settled bed and solid particles in the reactor; and
      cleaning and unplugging the filter bed to renew the filtration capacity of the filter bed by a method which consists only of rotation of the stirrer blade in the settled bed by a method comprising flowing liquid out of the blade through said openings in the blade.

2. The process of claim 1, wherein no motorized force is provided to the stirrer blade.

3. The process of claim 1 wherein an inlet stream to the vessel is provided, and the liquid above said settled bed has a higher concentration of suspended solids than the inlet stream.

4. The process of claim 1 wherein said stirrer blade operates intermittently to intermittently renew the filtration capacity of the settled bed.

5. The process of claim 1 wherein said stirrer blade operates continuously near the top of the settled bed.

6. The process of claim 1 wherein a plurality of said stirrer blades are provided at different levels within the reactor, wherein at least one of the stirrer blades is within said settled bed and at least one of the stirrer blades is above the settled bed.

7. The process of claim 6 wherein the fluid passing through said openings of one of said stirrer blades is different from the fluid passing through said openings of another of said stirrer blades.

8. The process of claim 6 wherein the stirrer blades both within and above said settled bed operate intermittently.

9. The process of claim 6 wherein the stirrer blade within said settled bed operates intermittently, and the stirrer blade above said settled bed operates continuously.

10. The process of claim 6 wherein the stirrer blades in both the settled bed and above said settled bed operate continuously.

11. The process of claim 1 further comprising remediation of waste, waste water, or contaminants by colonizing the solid particles by micro-organisms that remediate the waste, waste water, or contamination.

12. The process of claim 11, wherein no motorized force is provided to the stirrer blade.

13. The process of claim 11 wherein an inlet stream to the vessel is provided, and the liquid above said settled bed has a higher concentration of suspended solids than the inlet stream.

14. The process of claim 11 wherein the said stirrer blade operates intermittently.

15. The process of claim 11 wherein the said stirrer blade operates continuously near the top of the settled bed.

16. The process of claim 11 wherein a plurality of said stirrer blades are provided at different levels within the reactor, wherein at least one of the stirrer blades is within said settled bed and at least one of the stirrer blades is above the settled bed.

17. The process of claim 16 wherein the fluid passing through said openings of one of said stirrer blades is different from the fluid passing through said openings of another of said stirrer blades.

18. The process of claim 16 wherein the stirrer blades both within and above said settle bed operate intermittently.

19. The process of claim 16 wherein the stirrer blade within said settled bed operates intermittently, and the stirrer blade above said settled bed operates continuously.

20. The process of claim 16 wherein the stirrer blades in both the settled bed and above said settled bed operate continuously.

* * * * *